(12) United States Patent
Thijs et al.

(10) Patent No.: US 8,398,558 B2
(45) Date of Patent: Mar. 19, 2013

(54) AUTOMATIC TRANSMISSION POWER ADJUSTMENT FOR DOPPLER RADAR

(75) Inventors: Jeroen A. J. Thijs, Waldfeucht (DE); Robert Pinter, Aachen (DE); Jens Muehlsteff, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 253 days.

(21) Appl. No.: 13/002,731

(22) PCT Filed: Jul. 3, 2009

(86) PCT No.: PCT/IB2009/052915
§ 371 (c)(1),
(2), (4) Date: Jan. 5, 2011

(87) PCT Pub. No.: WO2010/004496
PCT Pub. Date: Jan. 14, 2010

(65) Prior Publication Data
US 2011/0125039 A1 May 26, 2011

(30) Foreign Application Priority Data
Jul. 11, 2008 (EP) .................................... 08160166

(51) Int. Cl.
*A61B 5/04* (2006.01)
*A61B 8/00* (2006.01)
*A61B 5/05* (2006.01)
(52) U.S. Cl. .................. 600/508; 600/455; 600/442
(58) Field of Classification Search .......... 600/453–457, 600/508, 509
See application file for complete search history.

(56) References Cited

U.S. PATENT DOCUMENTS

| 5,827,969 A * | 10/1998 | Lee et al. .................. 73/627 |
| 7,196,629 B2 | 3/2007 | Ruoss et al. |
| 7,917,209 B2 * | 3/2011 | Joo et al. ................... 607/6 |
| 8,135,462 B2 * | 3/2012 | Owen et al. ................ 607/6 |
| 8,142,361 B2 * | 3/2012 | Zhang et al. ............ 600/455 |
| 2007/0203417 A1 | 8/2007 | Wasserman et al. |
| 2008/0045832 A1 | 2/2008 | McGrath |
| 2008/0077015 A1 * | 3/2008 | Boric-Lubecke et al. .... 600/453 |
| 2009/0278728 A1 * | 11/2009 | Morgan et al. ........... 342/115 |

FOREIGN PATENT DOCUMENTS

| EP | 0064788 A | 11/1982 |
| WO | 2007063516 A | 6/2007 |
| WO | 2007143535 A | 12/2007 |
| WO | 2008017974 A | 2/2008 |
| WO | 2008102291 A | 8/2008 |

* cited by examiner

*Primary Examiner* — Brian T Gedeon
(74) *Attorney, Agent, or Firm* — W. Brinton Yorks, Jr.

(57) ABSTRACT

The invention relates to a Doppler radar heart sensor comprising a radar signal emitter (102); a radar signal receiver (103); a signal pattern matcher (106); and a transmission power adjuster (108). The signal pattern matcher (106) is connected to the radar signal receiver (102) and arranged to analyze a received radar signal (105), to compare the received radar signal with signal patterns, and to issue a corresponding indication signal upon detection of a sufficiently high similarity between the received radar signal and at least one of the signal patterns. A transmission power adjuster (109) is connected to the radar signal emitter (102) and the signal pattern matcher (106), the transmission power adjuster being arranged to gradually modify a transmission power delivered to the radar signal emitter (102) until the signal pattern matcher issues the indication signal. The invention also relates to a corresponding method and a computer program product.

14 Claims, 4 Drawing Sheets

AUTOMATIC TRANSMISSION POWER ADJUSTMENT FOR DOPPLER RADAR

FIELD OF THE INVENTION

The invention relates to the field of the detection of heart movement using Doppler radar technology. More particularly, the present invention relates to a Doppler radar heart sensor and a method for adjusting a transmission power of a Doppler radar heart sensor.

BACKGROUND OF THE INVENTION

Detecting and evaluating the activity and the health state of the heart is a common and important task for physicians and healthcare professionals in general. This applies to both, the human heart and the animal heart. There are currently several options for heart activity detection and evaluation. The ECG measurement has a long history in personal healthcare as the standard tool to assess the performance of a patient's electrical heart muscle excitation. More recent products give a patient insight in his cardiac stress level by heart rate variability analysis in small handheld devices. Still lacking today is a simultaneous detection of the ECG (electrical activation) and its translation into mechanical action by the heart muscle, which would enable a wide range of applications in clinical as well as in Personal Healthcare (PHC) scenarios. Problems in the mechanical heart motion analyzed together with the ECG information are related to cardiac stress and even serious cardio-vascular conditions. The pre-ejection period—defined as time difference of the ECG's Q-wave and aortic valve opening—has been found to be an indicator for mental stress in psychology (see for example the article by H. Boudoulas, et al., "Effect of increased Adrenergetic Activity on the Relationship Between Electrical and Mechanical Systole, Circulation 64, No. 1, 198, the disclosure of which being incorporated herein in its entirety) and is of particular relevance for blood pressure measurements based on the pulse wave methodology. For measurements of internal mechanical organ movements, state-of-the-art technologies are ultrasound, impedance cardiography, phonocardiography, or computed tomography (CT) and magnetic resonance tomography (MRT) imaging modalities. Most of these technologies are only applicable in PHC applications in a very limited number of cases. Some, like MR and CT are not applicable at all in PHC applications. Ultrasound measurements typically require trained personnel to position the probe over one of the windows that allow ultrasound to penetrate the body. Impedance cardiography requires the placement of several electrodes on a patient thorax, which is difficult for laymen. Although there are new upcoming opportunities with intelligent textiles, the effort for a spot measurement is still quite substantial. Phonocardiography is a well-established technique in the medical community and provides information via heart sounds on valve openings and closures as well as murmurs linked to serious conditions. In practice, it turns out that the placement of the microphones is rather difficult. Radar techniques have been investigated extensively for remote monitoring of a subject's heart rate and respiration rate in military and rescue applications. Furthermore, electromagnetic (EM) waves allow the registration of internal organ movements via the detection of the reflections at conductive boundary layers in the body. We have already shown that heart rate, breathing, vessel dilatation—suitable for pulse transit time measurements—and more sophisticated heart motion phases can be detected (see for example an article published by the inventors: J. Muehlsteff, et al. "The use of a two channel Doppler Radar Sensor for the detection of heart motion phases", 2006, IEEE EMBC 2006, conference proceedings). The present document concerns the use of a Doppler radar sensor, e.g. type KMY24, formerly available from Infineon, as described in the above mentioned article published by the inventors. The entirety of the article J. Muehlsteff, et al. "The use of a two channel Doppler Radar Sensor for the detection of heart motion phases", 2006, IEEE EMBC 2006, conference proceedings is incorporated herein by reference.

One of the problems that occur when a Doppler radar sensor is used for heart measurements with different subjects is the difference in body dimensions and the thickness of the layer of fat tissue. Body tissue has a high absorption coefficient for electromagnetic waves. Therefore, especially for overweight and obese subjects, the received Doppler radar signal is heavily attenuated. An increase in transmission power would compensate for this attenuation and would be required in order to have reliable diagnosable signals. However, increasing the power too much will render the sensor too sensitive and cause artifacts from movements outside the field of interest. Furthermore, in battery-powered applications, unnecessarily high power consumption should be avoided.

This application describes two embodiments that can be used to obtain maximal signal quality at the lowest possible electromagnetic radiation level and transmission power. It increases transmission power until a heart signal is recognized or makes use of external known movements to adjust transmission power to the optimal value.

SUMMARY OF THE INVENTION

It would be desirable to achieve a Doppler radar heart sensor that adapts the transmission power in such a way that it is appropriate to obtain the desired signal quality, but not higher than that, i.e. not higher than necessary. This strategy saves electric power, which is interesting in battery powered setups, and at the same time the patient exposure to electromagnetic radiation is minimized, whilst maintaining sufficient signal quality. It would also be desirable to enable a Doppler radar heart sensor to take into consideration the physical properties of the patient. To better address one or more of these concerns, in a first aspect of the invention a Doppler radar heart sensor is presented that comprises a radar signal emitter, a radar signal receiver, a signal pattern matcher, and a transmission power adjuster. The signal pattern matcher is connected to the radar signal receiver and arranged to analyze a received radar signal. The signal pattern matcher is also arranged to compare the received radar signal with signal patterns, and to issue a corresponding indication signal upon detection of a sufficiently high similarity between the received radar signal and at least one of the signal patterns. The transmission power adjuster is connected to the radar signal emitter and the signal pattern matcher. The transmission power adjuster is arranged to gradually modify a transmission power delivered to the radar signal emitter until the signal pattern matcher issues the indication signal.

The radar signal receiver may comprise an antenna and an amplifier. In addition, the radar signal receiver may comprise a Doppler analyzing portion that determines the amount of frequency shift between the emitted radar signal and the received radar signal. The radar signal emitter may comprise an antenna and an adjustable amplifier.

It would be further desirable to provide a Doppler radar heart sensor that can reliably distinguish a heart beat signal from signals coming from other sources. In an embodiment this concern is addressed by the signal pattern matcher comparing properties of the received radar signal with properties of typical heart beat signals. Heart rate and the shape of the detected movement are examples of such properties.

It would be further desirable to provide the Doppler radar heart sensor with a capability of directly comparing the received radar signal with signals that are known to correspond to heart activity. These signals that are known to correspond to heart activity could be pre-recorded, the recordings possibly covering several types of patients (stature, age, sex, health state, . . . ) and levels of patient activity (resting, walking, working out, . . . ).

Furthermore, it would be desirable to assist the determination of an optimal transmission power setting by providing a calibration. In an embodiment this concern is addressed by the signal patterns comprising Doppler radar sensed signals of known calibration movements in a coverage area of the radar signal receiver. A Doppler radar sensor reacts to movements in its coverage area. At least some of the properties of the known calibration movements are known in advance. Therefore it is a fairly simple task to identify their contribution to the received radar signal and/or a signal resulting from a comparison between the emitted radar signal and the received radar signal.

It would also be desirable to provide a Doppler radar heart sensor that is capable of performing the calibration movements for direct access to and/or control over the properties of the calibration movement. In an embodiment this concern is addressed by the Doppler radar heart sensor comprising a moving object for generating the known calibration movements. It should be noted that a physical connection is not necessary between the main component of the Doppler radar heart sensor and the moving object.

Furthermore, it would be desirable to provide a Doppler radar heart sensor that is capable of adjusting its transmission power in order to obtain a standard signal quality that is sufficient for subsequent analysis of the received signal. It would further be desirable to match the observed signal quality to the standard signal quality by means of a criterion that is representative or indicative of the signal quality. In an embodiment, these and other concerns are addressed by the Doppler radar heart sensor further comprising a memory for calibration signal quality measurements of a prior calibration session, wherein the signal pattern matcher determines a current signal quality and the transmission power adjuster stops modifying the transmission power when the current quality measurement is equal to or better than the calibration signal measurement.

It would also be desirable to provide a Doppler radar heart sensor that is capable of using information from other sources of information when determining the presence or absence of a detectable heart signal in a received radar signal. In an embodiment this concern is addressed by the Doppler radar heart sensor further comprising an electrocardiogram signal interface connected to the signal pattern matcher, wherein the signal pattern matcher compares the received radar signal also to a signal provided via the electrocardiogram interface.

Besides the Doppler radar heart sensor described above, it would be desirable to achieve a method for adjusting a transmission power of a Doppler radar heart sensor that adapts the transmission power in such a way that the power consumption of the setup is not higher than necessary, and the patient exposure to electromagnetic radiation is minimized, whilst maintaining sufficient signal quality. It would also be desirable that the method takes into consideration the physical properties of the patient. To better address one or more of these concerns, in a first aspect of the invention in a second aspect of the invention a method for adjusting a transmission power of a Doppler radar heart sensor is presented that comprises:

a) sending Doppler radar signals;
b) receiving a received radar signal;
c) analyzing the received radar signal;
d) comparing the received radar signal with signal patterns;
e) if said comparing reveals a sufficiently high similarity between the received radar signal and at least one of the signal patterns terminating the method for adjusting, or else adjusting the transmission power by gradually modifying the transmission power and the repeating actions a) to e).

It should be noted that after its termination, the method could be invoked again, based on a time schedule (e.g. every 10 seconds), based on operator interaction, or based on an on-going/intermittent analysis of the received radar signals during operation.

Furthermore, it would be desirable to provide a method for transmission power adjustment that avoids possibly harmful settings of the transmission power. In an embodiment this concern is addressed in that adjusting the transmission power comprises gradually increasing the transmission power from a low level to a level at which the sufficiently high similarity is detected.

It would also be desirable to provide a method for transmission power adjustment that reacts to changes in the signal quality and adjusts the transmission power such that a reasonable compromise between necessary signal quality and power consumption can be achieved. This has the additional advantage that the exposure of the patient to electromagnetic radiation is not higher than necessary. In an embodiment, these concerns are addressed in that adjusting the transmission power comprises gradually decreasing the transmission power from a previous high level to a level at which the similarity between the received radar signal and at least one of the signal patterns has a minimum admissible value.

Furthermore, it would be desirable to provide a method for transmission power adjustment that can reliably distinguish a heart beat signal from signals coming from other sources. In an embodiment this concern is addressed in that comparing the received radar signal with signal patterns comprises comparing properties of the received radar signal with properties of typical heart signals.

It would also be desirable to provide a method for transmission power adjustment that facilitates the determination of an optimal transmission power setting by providing a calibration. In an embodiment this concern is addressed by the method further comprising placing a moving object performing a known calibration movement in a coverage area of the Doppler radar heart sensor.

Furthermore, it would be desirable to provide a method for transmission power adjustment that is capable of obtaining a standard signal quality that is sufficient for subsequent analysis of the received signal. It would further be desirable to match the observed signal quality to the standard signal quality by means of a criterion that is representative or indicative of the signal quality. In an embodiment, these and other concerns are addressed by the method further comprising prior to action a): calibrating the Doppler radar heart sensor using a calibration object and a preselected transmission power to determine a calibration signal measurement. This calibration signal measurement represents one of the signal patterns in action e).

It would also be desirable to provide a method for transmission power adjustment that is capable of using information from other sources of information when determining the presence or absence of a detectable heart signal in a received radar signal. In an embodiment this concern is addressed by the method further comprising: receiving an electrocardiogram signal corresponding to electric activity of the heart and comparing the received radar signal with the electrocardiogram signal for determining whether the received radar signal corresponds to a heart beat caused by the electric activity of the heart.

It would be furthermore desirable to achieve a computer program that assists in finding an optimal transmission power setting for a Doppler radar heart sensor. To better address this concern and possible other concerns, in a third aspect of the invention a computer program is presented that enables a processor to carry out the method described above.

The different technical features can be arbitrarily combined and such combination is herewith disclosed. In particular, but not exclusively, a Doppler radar heart sensor may comprise any combination of the following: a radar signal emitter, a radar signal receiver, a signal pattern matcher, a transmission power adjuster, a moving object for generating known calibration movements, a memory for calibration signal quality measurements, and an electrocardiogram interface. In relation to a method for adjusting a transmission power of a Doppler radar heart sensor any combinations of the actions described above is possible and herewith disclosed. In particular, and by no means exclusively, two or more of the following actions can be combined:

sending Doppler radar signals;
receiving a received radar signal;
analyzing the received radar signal;
comparing the received radar signal with signal patterns;
if the comparison reveals a sufficiently high similarity between the received radar signal and at least one of the signal patterns terminating the method for adjusting, or else adjusting the transmission power by gradually modifying the transmission power and repeating the previous actions;
gradually increasing the transmission power from a low level to a level;
gradually decreasing the transmission power from a previous high level to a level at which the similarity between the received radar signal and at least one of the signal patterns has a minimum admissible value;
comparing properties of the received radar signal and at least one of the signal pattern has a minimum admissible value;
placing a moving object performing a known calibration movement in a coverage area of the Doppler radar heart sensor;
calibrating the Doppler radar heart sensor using a calibration object and a preselected transmission power to determine a calibration signal measurement;
receiving an electrocardiogram signal corresponding to electric activity of the heart and comparing the received radar signal with the electrocardiogram signal for determining whether the received signal corresponds to a heart beat caused by the electric activity of the heart.

The various embodiments may solve one or more of the following problems:

Maximal signal quality with minimal power consumption and exposure of the patient to electromagnetic radiation when using a Doppler radar sensor;

Minimization of the influence of external noise sources;

Adaptation of radiation power to the patient's thorax characteristics (dimension, fat).

These and other aspects of the invention will be apparent from and elucidated with reference to the embodiment(s) described herein after.

DETAILED DESCRIPTION OF THE EMBODIMENTS

Figure 1:
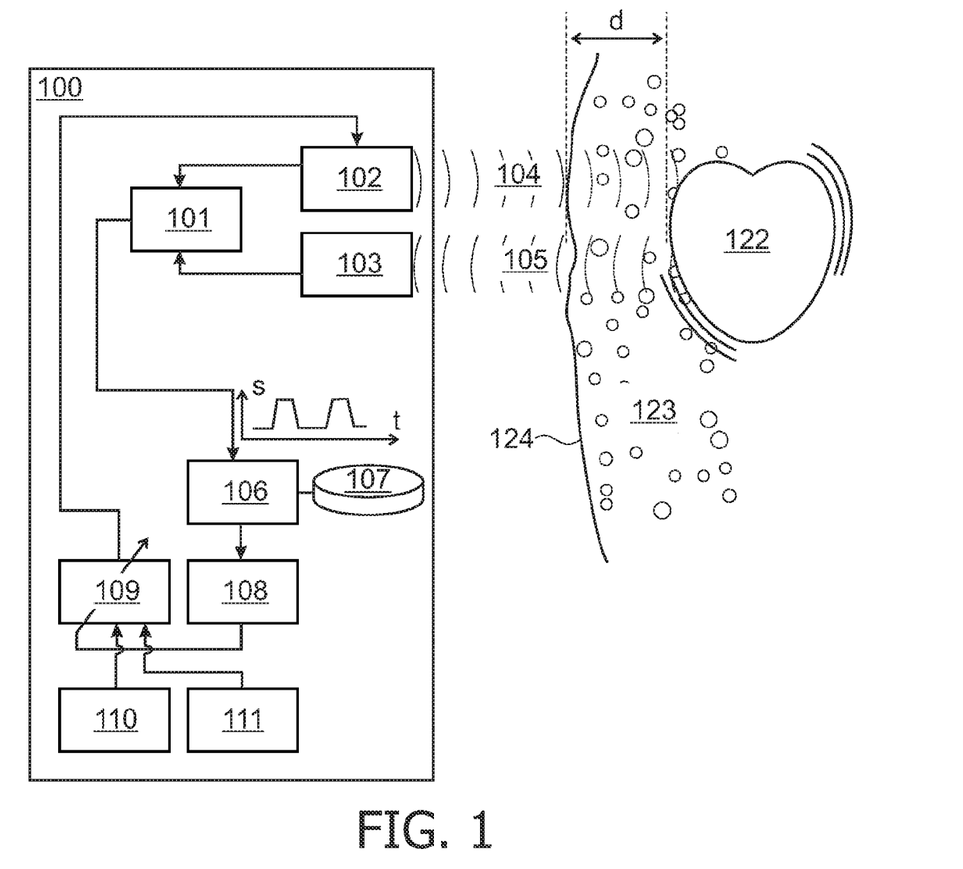
FIG. 1 shows a schematic block diagram of an embodiment of the invention.

FIG. 1 shows a schematic block diagram of an embodiment of the invention. A Doppler radar heart sensor 100 comprises a Doppler radar signal emitter 102 and a Doppler radar signal receiver 103. During operation, the Doppler radar signal emitter 102 emits a radar signal 104 in the direction of a chest of a human or an animal. The human chest is illustrated in a schematic view with a skin 124, body tissue 123, and the heart 122 of the patient. The heart 122 is situated at a certain depth beneath the skin 124 and this depth is illustrated in FIG. 1 and designated by the letter d. The heart depth d may vary significantly from one patient to another. For slim persons, depth d is rather small, while for big persons or obese persons d may take relatively high values.

The propagation properties of electromagnetic waves vary significantly in different body tissues. At a frequency of 2.4 GHz, the following properties are relevant:

| Tissue | Conductivity σ [S/m] | Rel. permeability $\epsilon_r$ | Loss tangent tan α | Wavelength λ [m] | Attenuation [m$^{-1}$] |
|---|---|---|---|---|---|
| Air | 0 | 1 | 0 | 0.12236 | 0 |
| Blood | 2.5448 | 58.264 | 0.3205 | 0.0158 | — |
| Bone | 0.39431 | 11.381 | 0.2542 | 0.0360 | — |
| Cartilage | 1.7559 | 38.277 | 0.3323 | 0.0194 | 31.9 |
| Fat | 0.10452 | 5.801 | 0.14524 | 0.053113 | 9.0 |
| Heart | 2.2561 | 52.714 | 0.3020 | 0.016346 | 38.7 |
| Muscle | 1.7388 | 52.729 | 0.2419 | 0.0167 | 31.7 |

One of the problems that occur when the Doppler radar sensor is used for thorax measurements with different subjects is the difference in body dimensions and the thickness of the body tissue layers. Several body tissues have a high absorption coefficient for electromagnetic waves. Therefore, especially for overweight and obese subjects, the received radar signal 105 is heavily attenuated. An increase in transmission power would compensate for this attenuation and would be required in order to have reliable diagnosable signals.

However, for subjects with thin layers of body tissue (slim or underweight subjects), an increased transmission would also increase the sensitivity of the radar sensor for the detection of unwanted organ movement or other movements around the body that are small but also in the field of view of the Doppler radar heart sensor. This means that in the case of a slim subject it is possible to operate the Doppler radar heart sensor with a much smaller power than in the case of an obese subject. An automatic adjustment of the transmission power according to what is really required helps to save electric power, which is interesting in particular, if the setup is powered from a battery. Additionally, patient safety is an important issue in medical systems. Concerns exist about the safety of electromagnetic radiation. If a Doppler radar sensor is used for heart or thorax measurements, electromagnetic radiation is transmitted and absorbed by body tissue. The effects of this absorption are under intensive investigation.

The Doppler radar heart sensor may also comprise a Doppler radar analyzer 101 that determines the amount of frequency shift between the emitted radar signal 104 and the received radar signal 105. From the determined amount of frequency shift in the field of view Doppler radar analyzer 101 may determine moving objects within the field of view and the degree/strength of movement. Doppler radar analyzer may be regarded as a part of radar signal receiver 103, but could be separate, as well.

Doppler radar analyzer 101 is connected to a signal pattern matcher 106 that receives signals corresponding to analyzing results from Doppler radar analyzer 101. An inset in FIG. 1 illustrates an exemplary analyzing result as a one-dimensional time variable signal s. Signal pattern matcher 106 is connected to a signal pattern storage 107 that contains prerecorded template signals corresponding to typical heart movements. Signal matching can be done e.g. by performing a cross-correlation between the analyzing result s and the plurality of signals stored in signal pattern storage 107.

At an output side, signal pattern matcher 106 is connected to a transmission power adjuster 108. The signal exchanged between signal pattern matcher 106 and transmission power adjuster can be an indication of e.g. whether the attained transmission power is sufficient, whether it is too low, or whether it is too strong. In dependence from this information, signal power adjuster 108 maintains, increases, or decreases the transmission power by changing operating parameters of for example a transmission power amplifier 109. Another option would be to change operating parameters of a digital-to-analogue converter, or to insert or bypass resistors by appropriate switching.

The power amplifier 109 is connected at one of its inputs to a microprocessor or -controller 110 of the Doppler radar heart sensor 100. Microprocessor 110 controls the operation of Doppler radar heart sensor 100. Another input of power amplifier 109 is connected to a power source 111, such as a switch-mode power supply or a battery.

An output of power amplifier 109 is connected to the radar signal emitter 102. Radar signal emitter 102 is supplied with electrical power either in bursts or in a continuous manner, depending on the selected operation mode for Doppler radar heart sensor 100.

Figure 2:
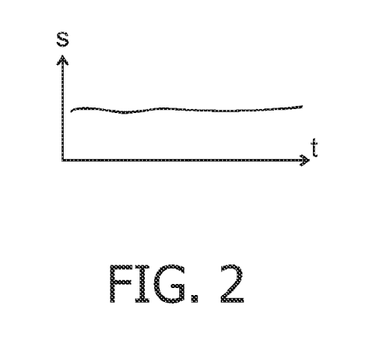
FIGS. 2 and 3 show diagrams of received radar signals over time without a visible heart beat (FIG. 2) and with a visible heart beat (FIG. 3).

FIG. 2 shows a diagram of a received radar signal over time without a visible heart beat. This can be interpreted as an indication that the transmission power is too weak. However, a missing visible heart beat could also be caused by a wrong positioning of the Doppler radar heart sensor or by a malfunction of a component. Under the assumption that the Doppler radar heart sensor is employed correctly and operational, the signal shown in FIG. 2 is interpreted as "transmission power too low" by signal pattern analyzer 108 (cf. FIG. 1). In FIG. 2 the transmission power is still too low and no heart signal is being picked up by the sensor, as the electromagnetic radiation is fully absorbed in the body tissue between sensor and heart wall.

Figure 3:
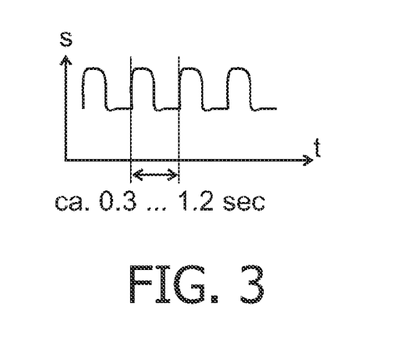

FIG. 3 is similar to FIG. 2, but this time a visible heart signal is present. The visible heart signal corresponds approximately to the contraction movement of the heart. One property of the heart signal is its frequency. The human heart usually beats between 50 and 200 times in a minute. Thus, the cycle time is between 0.3 and 1.2 sec. This knowledge can be used to distinguish the heart signal within the received radar signal. FIG. 3 shows the case where the transmission power is increased enough in order to penetrate the body tissue between sensor and heart wall. Transmission power is increased until a signal quality level is reached that has been preset. This can be preset using a reference measurement that has acceptable signal quality on another patient.

Figure 4:
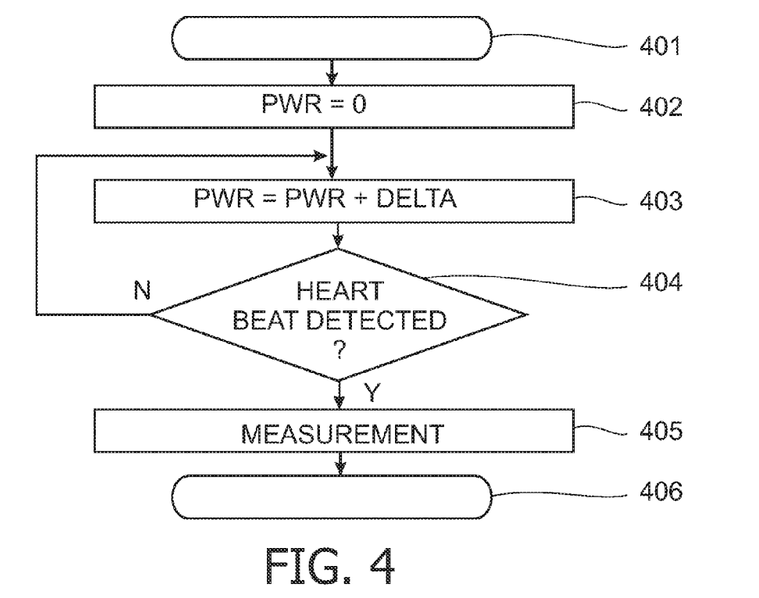
FIG. 4 shows a flow chart of a method according to an embodiment of the invention.

FIG. 4 shows a flow chart of a method according to a first embodiment. The method starts at action 401. In action 402 the transmission power is set to zero: "PWR=0". The transmission power is increased by a certain amount delta in action 403 "PWR=PWR+DELTA". An analysis of the received radar signal may be performed, depending on which a determination is made whether a heart beat could be detected "HEART BEAT DETECTED?" in action 404. If not, the method jumps back to action 403 to further increase the transmission power. If in action 404 a heart beat could be detected, the actual measurement of the heart movement begins in action 405. The method ends at action 406.

The loop between actions 403 and 404 actively adjusts the transmission power of the Doppler radar signal, depending on the body dimensions of the subject. There are two optimization actions possible. One optimization is to obtain a signal from many different subjects and body shapes without the need to attach other devices or additional hardware to the patient. In this case the signal quality is maintained at a level of signal quality, set by the user. The second optimization is for optimal signal-to-noise ratio. In this case, one or more additional known moving objects are attached to the patient as known 'noise' and it is ensured that the noise is minimal and the received signal from the heart is maximal.

In the scenario depicted in FIG. 4, the transmission power is gradually increased from 0 to a value where a heart beat signal can reliably be detected. This strategy ensures that a heart beat signal can be obtained from many different subjects and body shapes. The heart signal is detected by making use of its characteristics. Heart signals typically have frequency range of 50 to 180 $min^{-1}$ or 0.8 to 3 Hz. The beating of the heart furthermore has typical shape or cycle that can also be used. Typical characteristic points in the heart cycle as described in the above mentioned article by Muehlsteff et al. can be used to identify a heart beat signal. By using these characteristics, it is possible to distinguish signals originating from the heart's wall from surrounding movement signals. If the Doppler radar sensor is used in combination with an ECG measurement, the heart rate can be extracted from the ECG measurement and can be used to find the known heart rate signal in the Doppler signal output.

The method could be invoked again during the measurement in order to adjust the transmission power setting to changes that might have occurred in the meantime (e.g. due to a change in the measuring position of the Doppler radar heart sensor). In that case, action 402 could be skipped and the method would start at the current transmission power setting.

Figure 5:
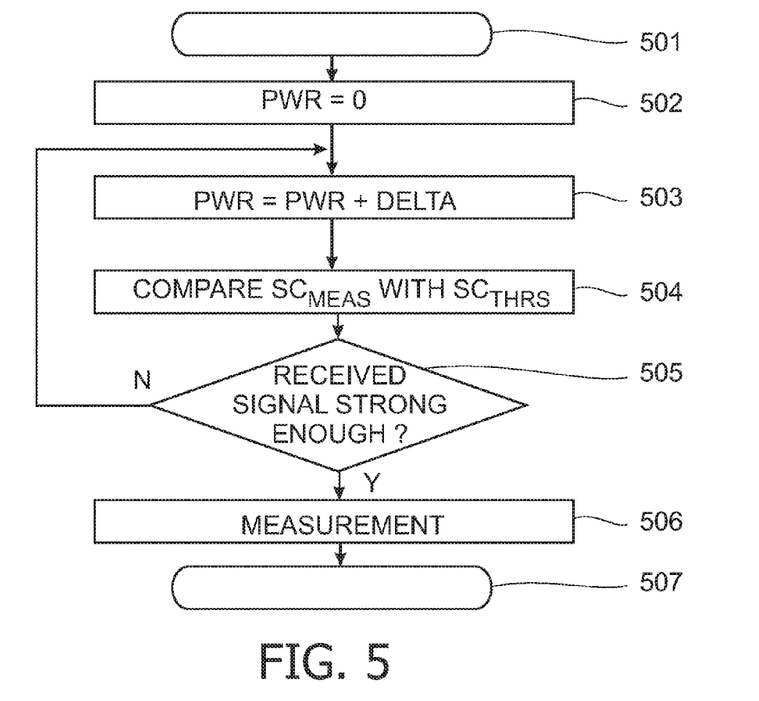
FIG. 5 shows a flow chart of a method according to another embodiment of the invention.

FIG. 5 shows a flow chart of a method according to a second embodiment. The method starts at action 501. The transmission power is set to zero in action 503 "PWR=0" and then increased by a certain amount "PWR=PWR+DELTA". Next, a signal quality criterion SC is measured. The measured value of the signal quality criterion $SC_{MEAS}$ is compared to a threshold value of the signal quality criterion $SC_{THRS}$ "COM- PARE $SC_{MEAS}$ WITH $SC_{THRS}$". If at branching point 505 it is determined that the comparison yields a result that indicates that the received signal is strong enough, then the actual measurement of heart movement is performed in action 506. In the contrary case, the method branches back to action 503 and the transmission power is further increased. The method ends at action 507.

As long as the transmission power is too low to penetrate the layer of fatty and muscle tissue, no heart signal will be detectable and transmission power has to be increased. As soon as a heart signal can be reliably detected, the right level of transmission power is reached and transmission power is no longer increased to avoid further noise signals. The criterion when a reliable and required quality of the heart signal is reached can be set by the user or someone else, depending on his application requirements. A measurement can be performed on slim persons and from that measurement the signal quality can be set.

Figure 6:
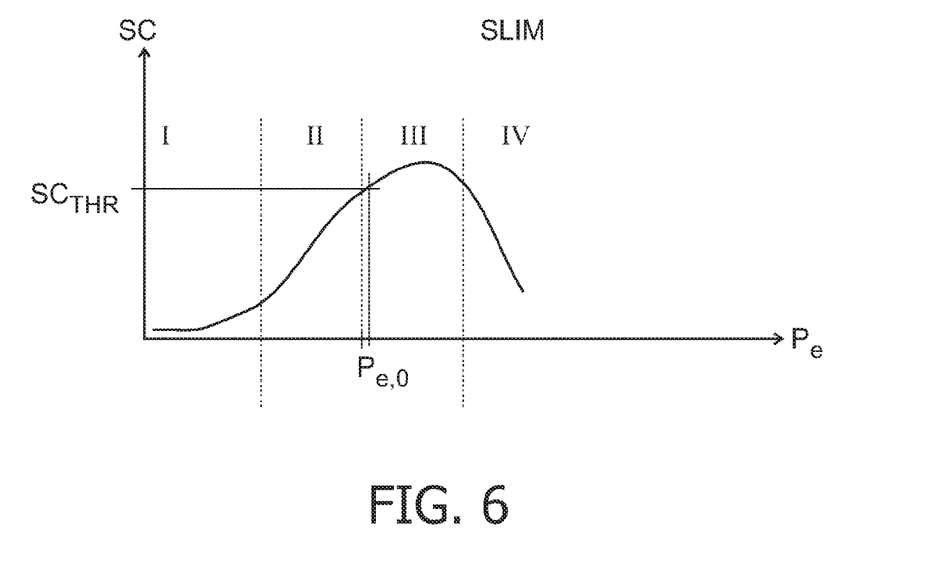
FIG. 6 shows a diagram illustrating a relation between signal quality and transmission power for a slim person.

FIG. 6 shows a diagram that illustrates the relation between the signal quality criterion mentioned in the discussion of FIG. 5 and the transmission power $P_e$. In FIG. 6 the relation is represented for a slim person, i.e. the emitted radar signal and the received radar signal are only lightly attenuated while travelling through the chest of the patient.

Figure 7:
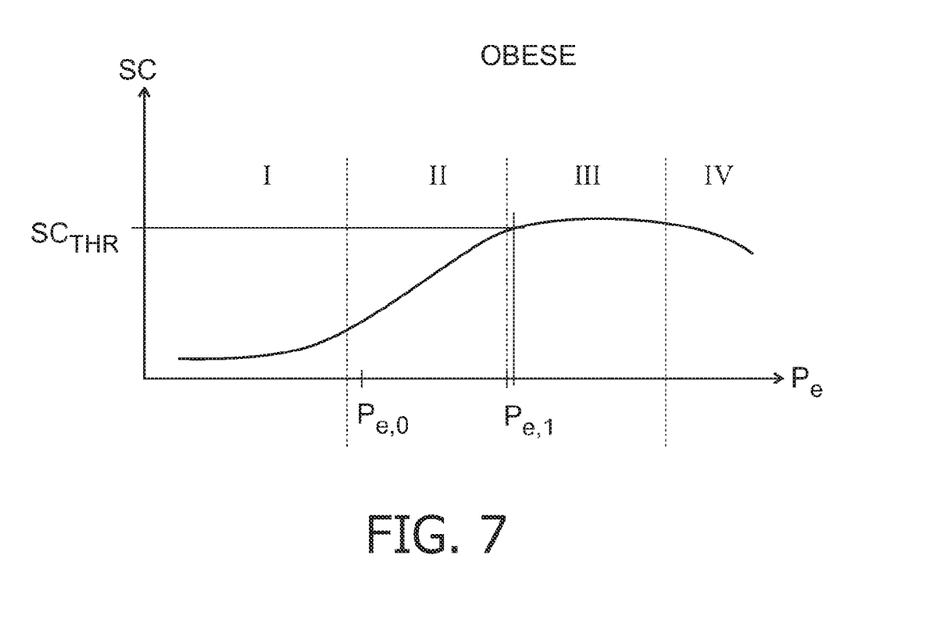
FIG. 7 shows a diagram illustrating a relation between signal quality and transmission power for an obese person.

Roughly, four main regions I to IV can be distinguished in the diagrams of FIGS. 6 and 7. In region I, the transmission power is so low that the emitted or at least the reflected signal is absorbed within the body tissue. Thus, no signal is detectable and the signal quality criterion SC is very low. In region II, the emitted signal reaches the heart and a signal is actually reflected by the heart. However, the received signal is still too weak for reliable detection. Nevertheless, a steep increase of the signal quality criterion SC can be observed in region II. Region III corresponds to the optimal region in which the emitted signal is strong enough to provoke a sufficiently strong reflected signal. In region IV however, the Doppler radar heart sensor may begin to pick up too many surrounding movements. This may lead to a degradation of the signal quality and the signal-to-noise ratio. Therefore the curve depicted in FIGS. 6 and 7 may actually decrease again in this region.

With reference to FIG. 6, the transmission power is set to a pre-selected value $P_{e,0}$ representing a minimal, yet sufficient transmission power. For a slim person it is assumed that the received heart signal will have a good signal quality, because of the weak attenuation of the signal on its way through the human chest. During a calibration session performed on a slim person, a threshold value for the signal quality criterion $SC_{THR}$ can thus be obtained.

Turning now to FIG. 7, the relation between signal quality criterion SC and transmission power $P_e$ for an obese person is illustrated. It can be seen that higher transmission powers are required in order to attain the same signal quality. i.e. the curve is shifted and stretched to the right. Furthermore, the curve might also be more flat, because more absorption takes place in the body tissue between the skin and the heart. If a signal quality is to be attained that corresponds to the threshold signal quality at $SC_{THR}$ (determined during a calibration session on a slim person, cf. FIG. 6), then the transmission power has to be chosen to be at a value $P_{e,1}$.

Figure 8:
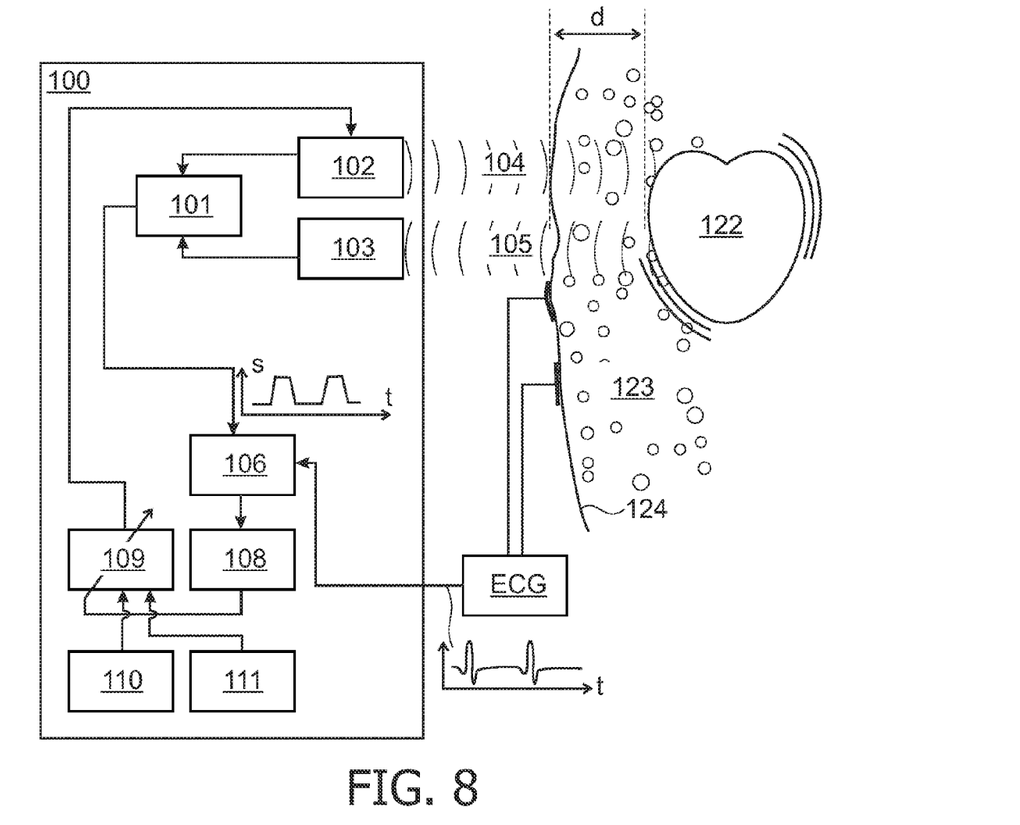
FIG. 8 shows a schematic bloc diagram of an embodiment of the invention.

FIG. 8 shows a block diagram of a Doppler radar heart sensor according to another embodiment. Those components that are similar or identical to the components illustrated and described in relation to FIG. 1 have the same reference signs. In this embodiment, signal pattern storage 107 is replaced by an input for an electrocardiogram signal. An electrocardiogram apparatus ECG is connected to the chest of the patient via two or more electrodes. The electrocardiogram apparatus ECG provides an electrocardiogram signal which is shown in the inset in FIG. 8. The electrocardiogram signal is provided to the Doppler radar heart sensor and forwarded internally to the signal pattern matcher 106. For the signal pattern matcher 106 the knowledge of the patient's electrocardiogram signal is a valuable piece of information, because it facilitates the detection of a heart signal within the received radar signal. In particular, the electrocardiogram signal may provide good estimates for the timing of the signal relative to the heart motion (usually slightly lagging behind the electrocardiogram signal). In further embodiments, the Doppler radar heart sensor may comprise both, a signal pattern storage 107 and an input for an electrocardiogram apparatus.

Figure 9:
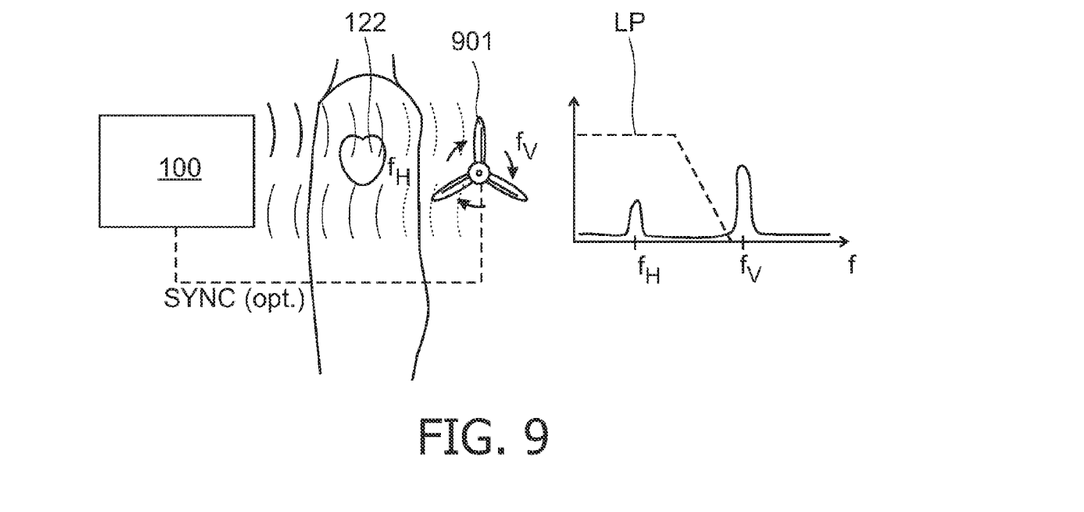
FIG. 9 shows an arrangement of a Doppler radar heart sensor, a patient and a moving object for calibration.

FIG. 9 shows an arrangement of a Doppler radar heart sensor 100, the chest of a patient, and a moving object 901. The moving object 901 moves at a frequency $f_V$ to create a calibration movement. Moving object 901 may be connected to the Doppler radar heart sensor 100 by a synchronization connection SYNC to provide Doppler radar heart sensor with accurate information about the movement performed by moving object 901, but this is optional. Also optional is a control connection between Doppler radar heart sensor 100 and moving object 901. As can be seen in FIG. 9, the radar signal emitted from Doppler radar heart sensor 100 travels through the body of the patient and traverses the heart 122. If the transmission power is strong enough, the emitted radar signal arrives at the patient's back where the moving object 901 is placed. Reflected signals from the moving object 901 are returned in the direction of the Doppler radar heart sensor. The right part of FIG. 9 shows the spectrum of the analyzed signal provided by Doppler radar analyzer 101. A distinctive peak can be expected at the frequency $f_V$. When the frequency of the calibration movement is chosen well above the typical frequency of the heart signal, then a low pass filter LP or a band pass filter can be applied that attenuates the contribution of the calibration movement in the received signal. As an alternative, the calibration movement can be switched off after successful calibration. The frequency $f_V$ is in fact much higher and not a multiple of the heart frequency $f_H$ so that its reflected signal can be distinguished from the heart signal. In this embodiment, the transmission power is increased to such a level, that the known frequency of the moving object $f_V$ can just be extracted from the received signal by means of a band-pass filter or a low pass filter. The sensitivity then reaches just up to the object and not farther. This ensures a very beneficial signal quality from the heart wall's reflection, whilst avoiding unnecessary high radiation levels, as well as unwanted reflections picked up from other objects around the patient.

In the scenario of FIG. 9 the transmission power is not adjusted according to a predefined quality criterion. However, the signal-to-noise ratio is optimized in such a way, that other moving objects that might be in the field of view of the sensor do not cause significant noise. The heart's reflection signal then has maximum signal strength. For this scenario additional known noise sources (moving objects) are added in the field of view of the sensor. The transmission power is then adjusted such that the reflections from these known objects do not significantly disturb the signal. In this scenario, the transmission power is high enough to get a heart signal, but not too high, thereby avoiding that the sensitivity of the sensor is increased to an unacceptable level.

While the invention has been illustrated and described in detail in the drawings and foregoing description, such illustration and description are to be considered illustrative or exemplary and not restrictive; the invention is not limited to the disclosed embodiments. For example, it is possible to operate the invention in an embodiment wherein the radar signal is emitted at another frequency than 2.4 GHz. The Doppler radar sensor might be capable of processing and producing two-dimensional or three-dimensional images of the field of view, roughly comparable to the images obtained from computer tomography or magnetic resonance imaging. The radar emitter and the radar receiver need not be in a single housing, but could be separate. Furthermore, also the analyzing circuitry and the power supply circuitry (including power amplifier 109) could be situated in a separate housing that may be placed on a desktop, on a stand, or the like. The ventilator that illustrates the moving object in FIG. 9 can be any type of moving object, such as a pendulum, or an oscillating object.

The invention can be used in all applications where the mechanical heart activity is measured to assess the pumping performance of the heart. This is additional information compared to the electrical excitation as measured using the ECG. Applications include the use of the sensor for gating purposes in imaging systems, where quiescent phases in the heart's pumping cycle have to be detected. This invention makes it possible to use the radar sensor for many different patients with different dimensions.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. Doppler radar heart sensor comprising:
   a radar signal emitter;
   a radar signal receiver;
   a signal pattern matcher connected to the radar signal receiver and arranged to analyze a received radar signal, to compare the received radar signal with signal patterns, and to issue a corresponding indication signal upon detection of a sufficiently high similarity between the received radar signal and at least one of the signal patterns;
   a transmission power adjuster connected to the radar signal emitter and the signal pattern matcher, the transmission power adjuster being arranged to gradually modify a transmission power delivered to the radar signal emitter until the signal pattern matcher issues the indication signal.

2. Doppler radar sensor according to claim 1, wherein the signal pattern matcher compares properties of the received radar signal with properties of typical heart beat signals.

3. Doppler radar heart sensor according to claim 1, wherein the signal patterns correspond to Doppler radar sensed signals of heart activity.

4. Doppler radar heart sensor according to claim 1, wherein the signal patterns comprise Doppler radar sensed signals of known calibration movements in a coverage area of the radar signal receiver.

5. Doppler radar heart sensor according to claim 4, further comprising a moving object for generating the known calibration movements.

6. Doppler radar heart sensor according to claim 1, further comprising a memory for calibration signal quality measurements of a prior calibration session, wherein the signal pattern matcher determines a current signal quality and the transmission power adjuster stops modifying the transmission power when the current signal quality measurement is equal to or better than the calibration signal measurement.

7. Doppler radar heart sensor according to claim 1, further comprising an electrocardiogram signal interface connected to the signal pattern matcher, wherein the signal pattern matcher compares the received radar signal also to a signal provided via the electrocardiogram interface.

8. Method for adjusting a transmission power of a Doppler radar heart sensor, the method comprising:
   a) sending Doppler radar signals;
   b) receiving a received radar signal;
   c) analyzing the received radar signal;
   d) comparing the received radar signal with signal patterns;
   e) if said comparing reveals a sufficiently high similarity between the received radar signal and at least one of the signal patterns terminating the method for adjusting, or else adjusting the transmission power by gradually modifying the transmission power and repeating actions a) to e).

9. Method according to claim 8, wherein adjusting the transmission power comprises gradually increasing the transmission power from a low level to a level at which the sufficiently high similarity is detected.

10. Method according to claim 8, wherein comparing the received radar signal with signal patterns comprises comparing properties of the received radar signal with properties of typical heart beat signals.

11. Method according to claim 8, further comprising placing a moving object performing a known calibration movement in a coverage area of the Doppler radar heart sensor.

12. Method according to claim 8, further comprising
   prior to action a), calibrating the Doppler radar heart sensor using a calibration object and a preselected transmission power to determine a calibration signal measurement;
   wherein the calibration signal measurement represents one of the signal patterns in action e).

13. Method according to claim 8, further comprising receiving an electrocardiogram signal corresponding to electric activity of the heart and comparing the received radar signal with the electrocardiogram signal for determining whether the received radar signal corresponds to a heart beat caused by the electric activity of the heart.

14. Computer program product comprising instructions that enable a processor to carry out the method of claim 8.

* * * * *